United States Patent [19]

Kitazume et al.

[11] Patent Number: 5,215,664
[45] Date of Patent: Jun. 1, 1993

[54] SEPARATION OF RARE EARTH ELEMENTS WITH HIGH-SPEED COUNTERCURRENT CHROMATOGRAPHY

[75] Inventors: Eiichi Kitazume, Rockville; Yoichiro Ito, Bethesda, both of Md.

[73] Assignee: The United States of America as represented by the Department of Health and Human Services, Washington, D.C.

[21] Appl. No.: 885,069

[22] Filed: May 18, 1992

Related U.S. Application Data

[63] Continuation of Ser. No. 485,317, Feb. 28, 1990, abandoned.

[51] Int. Cl.⁵ ............................................. B01D 15/08
[52] U.S. Cl. ................................... 210/635; 210/657; 436/82; 436/161; 436/164; 436/178; 423/21.5
[58] Field of Search ...................... 210/635, 657, 198.2, 210/656; 436/82, 161, 164, 178; 423/21.5

[56] References Cited

U.S. PATENT DOCUMENTS

| 3,077,378 | 2/1963 | Peppard | 423/21.5 |
|---|---|---|---|
| 3,784,467 | 1/1974 | Tanimura et al. | |
| 4,430,216 | 2/1984 | Ito | 210/511 |
| 4,461,748 | 7/1984 | Sabot et al. | 423/21.5 |
| 4,487,693 | 12/1984 | Ito | |
| 4,647,438 | 3/1987 | Sabot et al. | 423/21.5 |

FOREIGN PATENT DOCUMENTS

| 135456 | 8/1983 | Japan | 210/635 |
|---|---|---|---|
| 144745 | 8/1983 | Japan | 436/82 |

OTHER PUBLICATIONS

Ito, "Countercurrent Chromatography", *Journal of Biochemical and Biophysical Methods*, 5 (1981), pp. 105-129.

Ito, "Efficient Preparative Counter-Current Chromatography with a Coil Planet Centrifuge", *Journal of Chromatography*, 214 (1981), pp. 122-125.

Ito et al, "High-Speed Preparative Countercurrent Chromatography (CCC) with a Coil Planet Centrifuge", *Journal of Chromatography*, 224 (1982), pp. 247-258.

Ito et al, "Improved High-Speed Counter-Current Chromatography with Three Multilayer Coils Connected in Series", *Journal of Chromatography*, 475 (1989), pp. 219-227.

Ito et al, "Improved High-Speed Counter-Current Chromatograph with Three Multilayer Coils Connected in Series", *Journal of Chromatography*, 498 (1990), pp. 169-178.

Barkley et al, "Dynamic Chromatographic Systems for the Determination of Rare Earths and Thorium in Samples from Uranium Ore Refining Processes", *Analytic Chemistry*, 58 (1986), pp. 2222-2226.

Araki et al, "Separation of Lighter Rare Earth Metal Ions by Centrifugal Counter-Current Type Chromatograpby with Di-(2-Ethylhexyl)Phosphoric Acid", *Journal of Liquid Chromatography*, 11(1) (1988), pp. 267-281.

Akiba et al, "Mutual Separation of Lanthanoid Elements by Centrifugal Chromatography", *Journal of Liquid Chromatography*, 11(12) (1988), pp. 2517-2536.

Oka et al, "Improved Method for Continuous UV Monitoring in High-Speed Counter-Current Chromatography, *Journal of Chromatography*", 475 (1989), pp. 229-235.

Primary Examiner—Stanley S. Silverman
Assistant Examiner—Neil M. McCarthy
Attorney, Agent, or Firm—Lowe, Price, LeBlanc & Becker

[57] ABSTRACT

A method of separating rare earth elements and compounds from mixtures containing the same which comprises separating the rare earth elements and compounds by means of rotational high speed countercurrent chromatography.

15 Claims, 8 Drawing Sheets

SEPARATION OF RARE EARTH ELEMENTS WITH HIGH-SPEED COUNTERCURRENT CHROMATOGRAPHY

This application is a continuation application of application Ser. No. 07/485,317, field Feb. 28, 1990, now abandoned.

TECHNICAL FIELD

The present invention relates to continuous countercurrent chromatography, and more particularly relates to methods for continuous countercurrent chromatography separation and detection of rare earth elements and compounds.

BACKGROUND ART

High speed countercurrent chromatography (CCC) has been widely used for separating various organic compounds.

Performance of preparative CCC systems mainly depends upon the amount of the stationary phase retained in the column, which determines both the resolving power of the solute peaks and the sample loading capacity. Various CCC systems developed in the past (see Y. Ito, J. Biochem, Biophys. Met., 5 (1981) 105) are usually capable of yielding retention of the stationary phase of no more than 50% of the total column space. This maximum attainable retention level tends to fall rather sharply with the application of higher flow rates of the mobile phase, resulting in loss of peak resolution. Consequently, the applicable flow rate has become one of the major limiting factors in CCC, and the methods require relatively long separation times ranging from overnight to several days to complete a sizable separation.

As a result of efforts made to develop a new CCC system which performs efficient extraction under a high feed rate of the sample solution, it has been found that the use of a multiple-layer coiled column (a coiled tube wound on a reel) becomes ideal for performing preparative CCC, for example, as demonstrated on a preliminary separation of DNP amino acids with a conventional two-phase solvent system (See Y. Ito, J. Chromatogr., 214 (1981) 122). Because of the high flow rate of the mobile phase, this system can provide efficient chromatographic separation on a preparative scale within several hours.

U.S. Pat. No. 4,430,216 to Ito discloses an improved countercurrent chromatography system which utilizes planetary motion to establish a hydrodynamic equilibrium between two immiscible solvent phases. This CCC system enables short separation times.

CCC systems have been widely used to separate various organic compounds. However, there remains a need for a chromatography method which can efficiently separate rare earth elements and compounds.

DISCLOSURE OF THE INVENTION

It is accordingly one object of the present invention to provide a method for separating inorganic elements from mixtures containing the same.

It is another object of the present invention to provide a method for high speed countercurrent chromatography separation of inorganic elements.

It is a further object of the present invention to provide a method for separating rare earth elements and compounds.

It is a still further object of the present invention to provide a method for detecting rare elements and compounds in mixtures.

It is a still further object of the present invention to provide a method for high speed countercurrent chromatography separation of rare earth elements and compounds.

It is a still further object of the present invention to provide a method for continuous monitoring of high speed countercurrent chromatography.

According to the present invention there is provided a method of separating rare earth elements and compounds from mixtures containing the same which comprises separating said rare earth elements and compounds by means of rotational high speed countercurrent chromatography.

Also provided by the present invention is a method for analyzing for rare earth elements and compounds in a mixture containing the same which comprises separating said rare earth elements and compounds by means of rotational high speed countercurrent chromatography and continuously detecting for eluted rare earth elements and compounds.

BRIEF DESCRIPTION OF DRAWINGS

Aspects of the present invention will be described with reference to the annexed drawings, which are given by way of non-limiting examples, in which:

FIGS. 1-8 are chromatograms of various samples separated by the method of the present invention.

BEST MODE FOR CARRYING OUT THE INVENTION

Figure 1A:
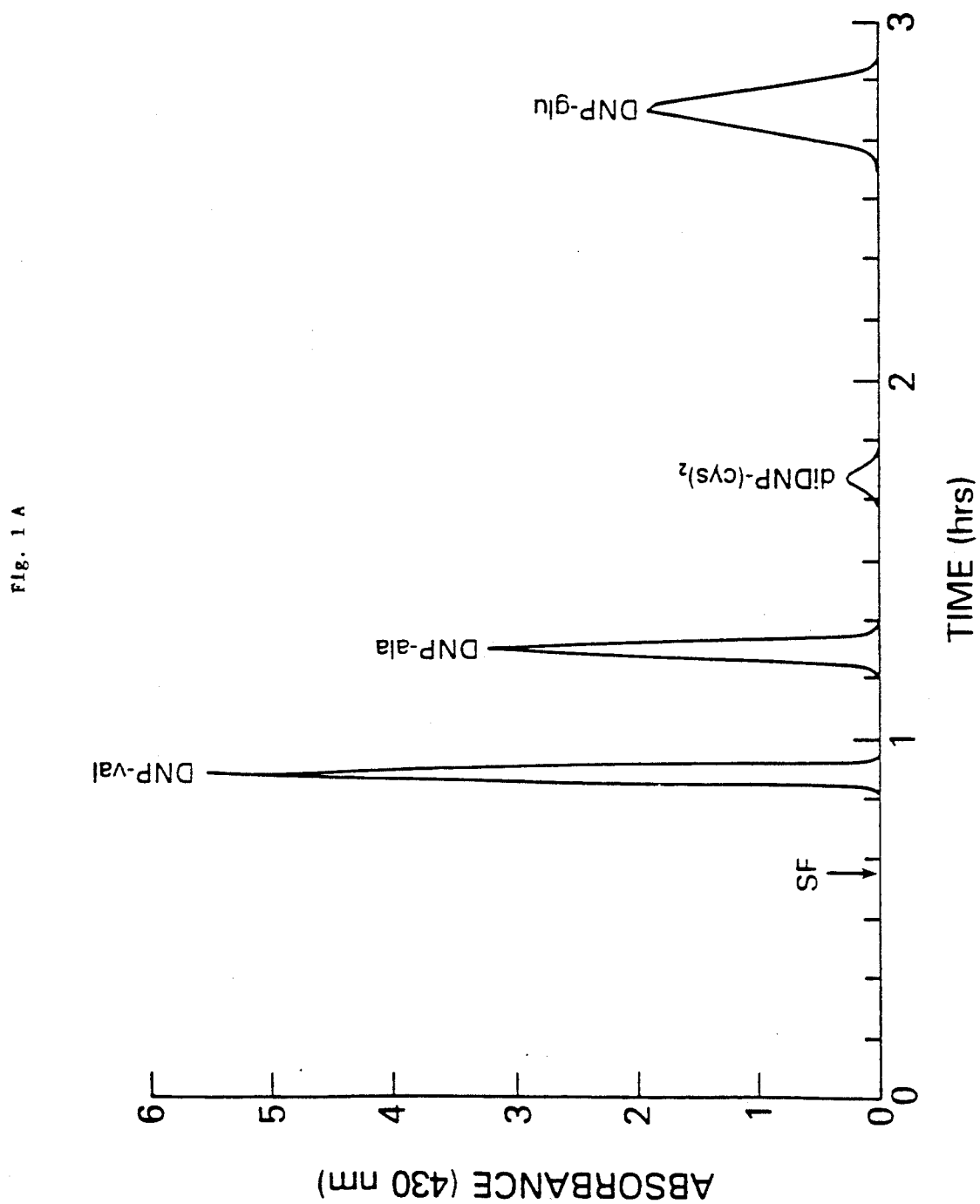

Recently, a high-speed CCC centrifuge equipped with a set of three multilayer coils connected in series has been developed and disclosed in U.S. Pat. No. 4,430,216 to Ito. This disclosed system has given the expected threefold increase in both partition efficiency and sample loading capacity as demonstrated in semi-preparative separations with multilayer coils of 1 6 mm I.D. and a total capacity of 400 ml.

In the present invention, the capability of the Ito system has been further extended by the use of a smaller-bore column (1 mm I.D.) connected in series. Highly efficient chromatographic separations were demonstrated with a variety of testing samples ranging from submilligram to 100 mg, including DNP amino acids, indole auxins, tetracycline derivatives, bacitracin, flavonoids from *Hippophae rhamnoides*, triterpenoic acids from *Boswellia carterii*, and rare earth elements each with a suitable two-phase solvent system.

The design of the apparatus employed in the present invention is described in U.S. Pat. No. 4,430,216, to Ito, incorporated herein by reference, and therefore only a brief statement is given here.

The apparatus holds a set of three identical columns symmetrically on the rotary frame at a distance of 7.5 cm from the central axis of the centrifuge. Each column holder is equipped with two planetary gears, one of which engages to an identical stationary sun gear mounted around the central stationary pipe of the centrifuge. This gear arrangement produces a desired planetary motion of each column holder, i.e., one rotation about its own axis per one revolution around the central axis of the centrifuge in the same direction. The other gear on the column holder is engaged to an identical gear on the rotary tube support mounted between the column holders. This gear engagement produces counterrotation of the tube support to prevent twisting of the flow tubes on the rotary frame.

All column holders can be removed from the rotary frame by loosening a pair of screws on each bearing block, thus facilitating the mounting of the coiled column on the holder. Each multilayer coil was prepared from a single piece of approximately 100 m long, 1.07 mm I.D. PTFE (polytetrafluoroethylene) tubing (Zeus Industrial Products, Raritan, NJ) by winding it directly onto the holder hub (7.5 cm diameter), making 13 layers of the coil between a pair of flanges spaced 5 cm apart.

The beta value ranged from 0.5 at the internal terminal to 0.75 at the external terminal. (Beta is an important parameter used to determine the hydrodynamic distribution of the two solvent phases in the rotating coil. $\beta = r/R$, where r is the distance from the column holder axis to the coil and R, the distance from the holder axis to the axis of the centrifuge).

Each multilayer coil consists of about 400 helical turns with an approximately 90 ml capacity. In order to prevent dislocation of the multilayer coil on the column holder, the innermost layer of the coil was glued onto the holder hub with an RTV silicone rubber adhesive sealant (General Electric Company, Waterford, NY, USA) while the whole column and the peripheral portion of the flanges were wrapped with a heat shrinkable PVC tube.

Each terminal of the multilayer coil was connected to a flow tube, 0.55 mm I.D. and 0.45 mm wall thickness. The use of this thick-wall, small-bore tubing is required at the flexing portion of the flow tube to withstand the back pressure created from the long narrow-bore semianalytical columns. Serial connection between the three multilayer coils was made in such a way that the internal terminal of the first column is connected to the external terminal of the second column, and the internal terminal of the second column is attached to the external terminal of the third column. In this way, all three columns are subjected to the same head-tail elution mode. As previously described, each interconnection flow tube runs across the rotary frame along the rotary tube support where it is secured with nylon ties. Each flexing portion of the flow tubes is lubricated with grease and protected with a sheath of Tygon tubing to prevent direct contact with metal parts. Both inlet and outlet flow tubes are secured on the centrifuge wall each with a silicone-rubber-padded clamp.

The apparatus can be operated at the maximum revolutional speed of 1,500 rpm with a speed control unit. Based on the rotation of the apparatus, the method of the present invention which utilizes the apparatus is appropriately referred to as rotational high speed countercurrent chromatography. A Beckman Accu Flo pump was used to pump the solvents. Continuous UV monitoring was performed with an LKB 2138 Uvicord S UV monitor (LKB. Bromma, Sweden) and a Pharmacia 482 recorder (Pharmacia, Uppsala, Sweden) and an LKB fraction collector (Ultrorac) to fractionate the effluent. On the flow line between the coiled column and the UV monitor, a fine PTFE tube of 3 m ×0.46 mm I.D. (Zeus, Raritan, NJ, USA) was inserted, which was heated in a water bath at a desired temperature. A similar tube was also applied at the outlet of the UV monitor to prevent a sudden pressure drop which would generate gas bubbles from the mobile phase. This arrangement of the two tubes in a heated waterbath eliminated turbidity of the thermolabile mobile phase in the UV flow cell and generation of gas bubbles, thus stabilizing the continuous UV monitoring.

Organic solvents, including n-heptane, n-hexane, chloroform, ethyl acetate, n-butanol, and methanol, were glass-distilled chromatographic grade, obtained from Burdick and Jackson Laboratories, Inc., Muskegon, MI. USP 95% ethanol was obtained from Warner-Graham Company, Cockeysville, MD. Di-(2-ethylhexyl) phosphoric acid (DEHPA) was obtained from Sigma Chemical Co., St. Louis, MO. Ammonium acetate and 1 N hydrochloric acid were obtained from Fisher Scientific Company, Fair Lawn, NJ. Arsenazo III was obtained from Aldrich Chemical Company, Milwaukee, WI.

Various testing samples used in the present invention are listed in Table 1 below.

TABLE 1

Summary of Experimental Conditions

| Sample | Solvent System | | | Mobile Phase | Flow Rate (ml/h) | Revolution (rpm) | Pressure (psi) | Retention (%) |
|---|---|---|---|---|---|---|---|---|
| DNP amino acids | | | | | | | | |
| DNP-L-valine (DNP-val) | 2.4 mg | chloroform | 2 | lower | 180 | 1250 | 255 | 57.7 |
| DNP-L-alanine (DNP-ala) | 2.4 mg | acetic acid | 2 | nonaqueous | | | | |
| diDNP-L-cystine (diDNP-(cys)$_2$) | 0.5 mg | 0.1 M hydro- | 1 | | | | | |
| DNP-D,L-glutamic acid (DNP-glu) | 4.8 mg | chloric acid | | | | | | |
| DNP amino acids | | | | | | | | |
| DNP-L-aspartic acid (DNP-asp) | 2.4 mg | chloroform | 2 | upper | 180 | 1250 | 90** | 41.5 |
| DNP-D,L-glutamic acid (DNP-glu) | 2.4 mg | acetic acid | 2 | aqueous | | | | |
| diDNP-L-cystine (diDNP-(cys)$_2$) | 0.5 mg | 0.1M hydro- | 1 | | | | | |
| DNP-L-alanine (DNP-ala) | 4.8 mg | chloric acid | | | | | | |
| Indole auxins | | | | | | | | |
| indole-3-acetamide (IA) | 10 mg | n-hexane | 1 | lower | 150 | 1250 | 220 | 53.3 |
| indole-3-acetic acid (IAA) | 30 mg | ethyl acetate | 1 | aqueous | | | | |
| indole-3-butyric acid (IBA) | 30 mg | methanol | 1 | | | | | |
| indole-3-acetonitrile (IAN) | 30 mg | water | 1 | | | | | |
| Tetracycline derivatives | | | | | | | | |
| oxytetracycline (OTC) | 10 mg | ethyl acetate | 1 | lower | 150 | 1250 | 220 | 54.0 |
| chlortetracycline (CTC) | 20 mg | n-butanol | 1 | aqueous | | | | |
| doxycycline (DC) | 20 mg | 0.25 M ammonium acetate | 2 | | | | | |
| Rare earth elements | | | | | | | | |
| lanthanum chloride (LaCl$_3$) | 25 μg | 0.02 M DEHPA* | 1 | lower | 300 | 900 | 300 | 36.2 |
| praseodymium chloride (PrCl$_3$) | 25 μg | in n-heptane | | aqueous | | | | |
| neodymium chloride (NdCl$_3$) | 25 μg | 0.02 M hydrochloric acid | 1 | | | | | |

TABLE 1-continued

| Sample | Solvent System | | Mobile Phase | Flow Rate (ml/h) | Revolution (rpm) | Pressure (psi) | Retention (%) |
|---|---|---|---|---|---|---|---|
| Flavonoids (sea buckthorn extract) | 100 mg chloroform methanol water | 4 3 2 | lower nonaqueous | 180 | 1200 | 300 | 60.0 |
| Bacitracin | 100 mg chloroform 95% ethanol water | 5 4 3 | lower nonaqueous | 150 | 1200 | 220 | 50.0 |
| Triterpenoic acids (*Boswellia carterii* extract) | 100 mg n-hexane 95% ethanol water | 6 5 1 | lower aqueous | 150 | 1200 | 300 | 57.8 |

*di(2-ethylhexyl) phosphoric acid;
**The tail-to-head elution mode resulted in a low back pressure.

DNP amino acids, indole auxins, tetracycline derivatives and bacitracin were all obtained from Sigma Chemical Company. Lanthanum chloride anhydrous, praseodymium chloride heptahydrate, and neodymium chloride hexahydrate were obtained from Aldrich Chemical Company. The triterpenoic acid sample was obtained from the extract of *Boswellia carterii* (Burseraceae). The crude sea buckthorn (*Hippophae rhamnoides*) ethanol extract (dried powder) was obtained from China by the courtesy of Professor Tian-You Zhang of Beijing Institute of New Technology Application, Beijing, China.

Two-phase solvent systems employed in the present studies are listed in Table 1. Each solvent mixture was thoroughly equilibrated in a separatory funnel by repeated vigorous shaking and degassing several times at room temperature. For preparation of the two-phase solvent system for the rare earth element separation, DEHPA was first washed 5 times with 1 M hydrochloric acid and then washed twice with distilled water before being dissolved in heptane.

Various testing samples selected for the present studies are also listed in Table 1 together with two-phase solvent systems used for separation. The sample solution for each separation was prepared by dissolving the sample mixture in 0.2 to 5 ml of the upper and/or the lower phases which were used for the separation.

Most of the separations were performed according to a standard method as follows: The separation column was first entirely filled with the stationary phase. This was followed by injection of the sample solution through the sample port. Then, the mobile phase was pumped into the column at a desired flow rate of 2.5-3 ml/min in the proper head-tail elution mode while the centrifuge was run at the desired revolutional speed. The effluent from the outlet of the column was continuously monitored with an LKB Uvicord S at 278 nm and fractionated with an LKB fraction collector.

In the separation of the rare earth elements, the column was first fully equilibrated with the mobile phase (0.02M HCl) before the sample charge. The on-line detection of the metal ions was effected by means of the post-column reaction with arsenazo III. The effluent from the column was divided into two streams with a tee adapter and a low-dead-volume Shimadzu LC-6A pump. At the outlet of the pump, the arsenazo III ethanol solution (0.014%, w/v) was continuously added to the effluent stream at a rate of nearly two parts to one part of the effluent with a Rainin metering pump (Rainin Instrument Co., Woburn, MA).

The colored effluent was first passed through a narrow mixing coil (0.55 mm I.D. ×1 m) which was immersed into a water bath heated to 40° C. and then led through an analytical flow cell (1 cm light path) of a Shimadzu SPD-6AV spectrophotometer to monitor the absorbance at 650 nm. The other effluent stream through the tee adapter can be fractionated with a fraction collector or discarded.

Except for the rare earth elements, the fractions obtained from each separation were manually analyzed for determination of absorbance to draw an elution curve. An aliquot of collected fractions was mixed with a known volume of methanol or water (when the fractions contained salt), and the absorbance was measured at an optimum wavelength (430 nm for DNP-amino acids, 280 nm for indole auxins, 350 nm for tetracycline derivatives, 260 nm for flavonoids, 250 nm for bacitracin, and 210 nm for triterpenoic acids) with a Zeiss PM6 spectrophotometer.

From the obtained chromatograms, partition efficiency of the separation was computed and expressed in terms of theoretical plates (TP) according to the conventional gas chromatographic equation $$N = (4R/W)^2 \tag{1}$$

where N is the number of theoretical plates, a measurement of partition efficiency; R, the retention time or volume of the peak maximum; and W, the peak width expressed in the same unit as R.

The partition efficiency can also be expressed in terms of peak resolution according to the following formula:

$$R_s = 2(R_1 - R_2)/(W_1 + W_2) \tag{2}$$

where $R_s$ is the resolution of the adjacent two peaks expressed in the unit of $4\delta$ in a Gaussian distribution; $R_1$ and $R_2$, the retention time (or volume) of the two adjacent peaks ($R_1 > R_2$); and $W_1$ and $W_2$, the width ($4\delta$) of the corresponding peaks. When $R_s = 1.5$, it represents a baseline separation (99.7% pure).

The capability of the present apparatus was evidenced in semianalytical separations of various test samples with a variety of two-phase solvent systems. These testing samples may be divided into two categories, i.e., the synthetic mixtures for evaluation of the partition efficiency and for comparative studies; and the natural products samples with a wide range of polarities for evaluation of the system in natural product research. The successful separation of lanthanoids ($La^{+3}$, $Pr^{+3}$, and $Nd^{+3}$) further proved the present system's capability in resolving inorganic and organic elements.

In addition to separating rare earth elements and compounds, the present invention may be utilized to separate any other metal or compound thereof including inorganic and organic compounds.

EXAMPLE 1

In this example, two sets of DNP amino acid mixtures were selected, one for the lower nonaqueous phase as the mobile phase and the other for the upper aqueous phase as the mobile phase. One component, diDNP-(cys)$_2$ contained in both sample mixtures, is a submilligram quantity and constitutes 5% of the total mass to serve as a reference compound for recovery rate of minor components.

Figure 1B:
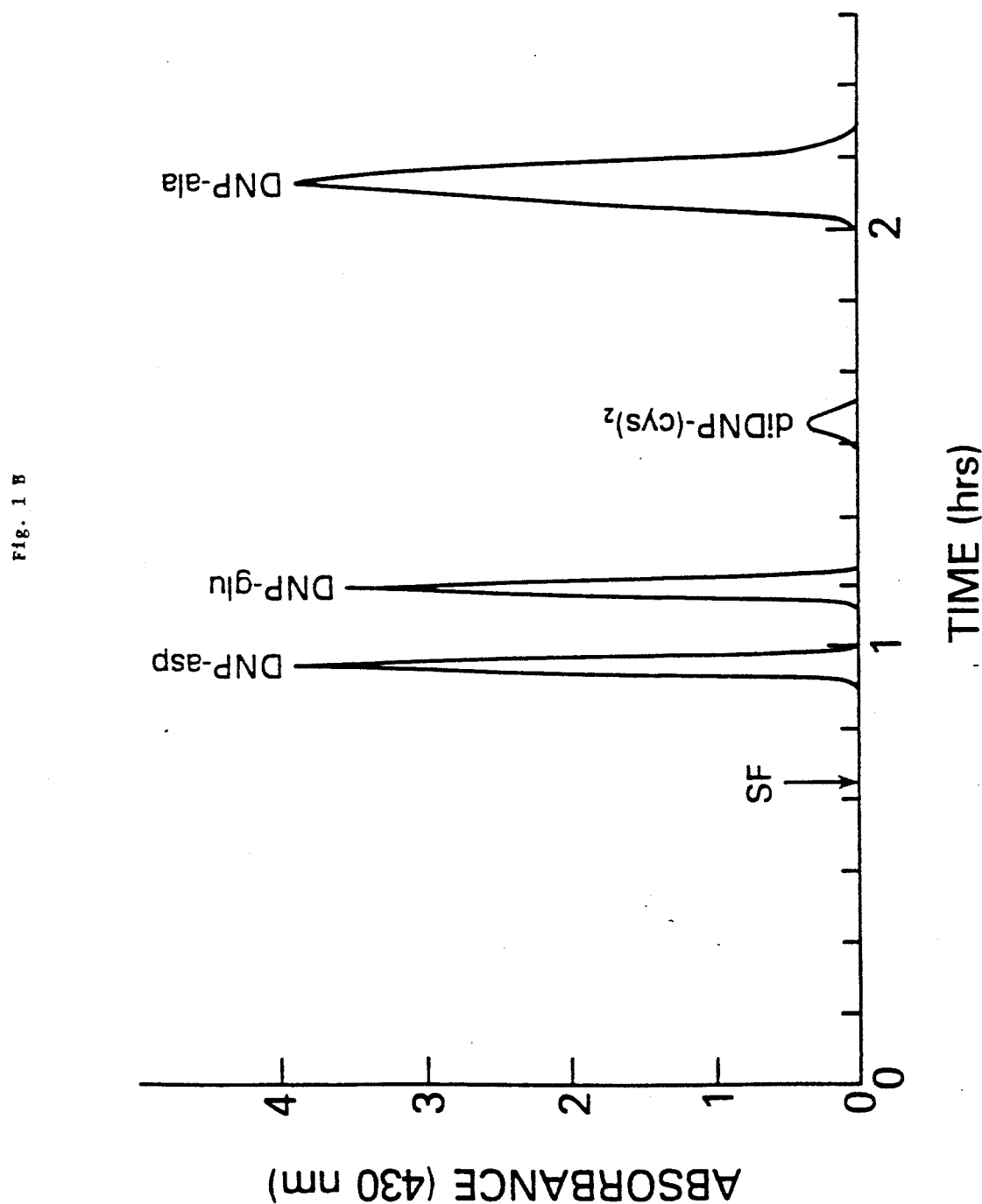

FIGS. 1A and 1B show the chromatograms of DNP amino acids obtained with a two-phase solvent system composed of chloroformacetic acid-0.1 M hydrochloric acid (2:2:1, v/v/v). In FIG. 1A, the lower phase was employed as the mobile phase, while in FIG. 1B the upper phase was used as the mobile phase. Both separations were performed at a flow rate of 180 ml/h at 1,250 rpm. In each test, a 10 mg quantity of sample mixture dissolved in 1 ml of the stationary phase was efficiently separated into four symmetrical peaks within 3 hours. The partition efficiencies estimated from Eq. 1 range from 3,000 to 5,000 TP, which are substantially greater than 1,200–3,500 TP obtained from the semipreparative column of 1.6 mm I.D. used in previous studies. The multilayer coils used in the present studies consist of about 1,200 helical turns of a 300 m length of tubing, thus yielding an average of 3.5 TP per turn or a 7.5 cm length for one TP. These figures are quite comparable to those obtained from the semipreparative column.

EXAMPLE 2

Figure 2:
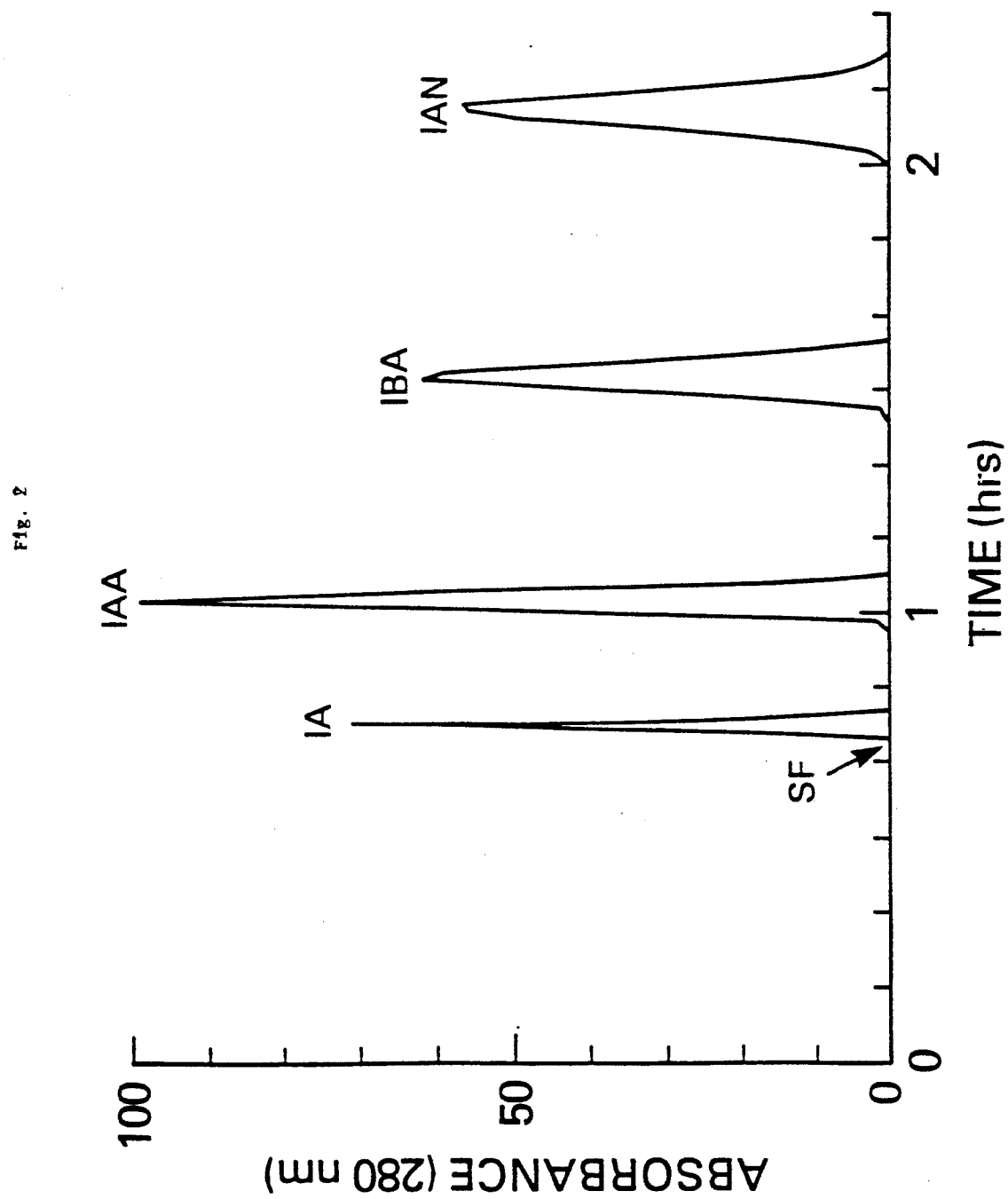

In this example, separation of indole auxin was performed by eluting the lower aqueous phase at a flow rate of 150 ml/h under a revolutional speed of 1,250 rpm. A 100 mg quantity of the sample mixture dissolved in 2 ml of the two-phase mixture was efficiently separated in slightly over 2 hours with partition efficiencies ranging from 2,500 to 4,500 TP which show a substantial improvement over 1,200–3,500 TP obtained from the 1.6 mm I.D. semipreparative column. FIG. 2 shows a chromatogram of indole auxins obtained with a two-phase solvent system composed of n-hexane-ethyl acetate-methanol-water (1:1:1:1, v/v/v/v).

This solvent system has a special advantage in that it can be applied to a variety of samples with a wide range of hydrophobicity simply by modifying the volume ratio between n-hexane and ethyl acetate. All these solvent systems provide a satisfactory retention of the stationary phase in the multilayer coil and permit a stable uv trace of the elution curve on the recorder.

EXAMPLE 3

In this example, tetracycline derivatives were separated. The separation of the tetracycline derivatives is greatly affected by the composition of the aqueous phase. The use of a salt-free solvent system such as ethyl acetate-n-butanol-water (3:2:5) produced extremely broad peaks, for CTC (second peak) and DC (third peak). However, an addition of 0.25 M ammonium acetate or neutral sodium phosphate to the aqueous phase remarkably improved the partition efficiency.

Figure 3:
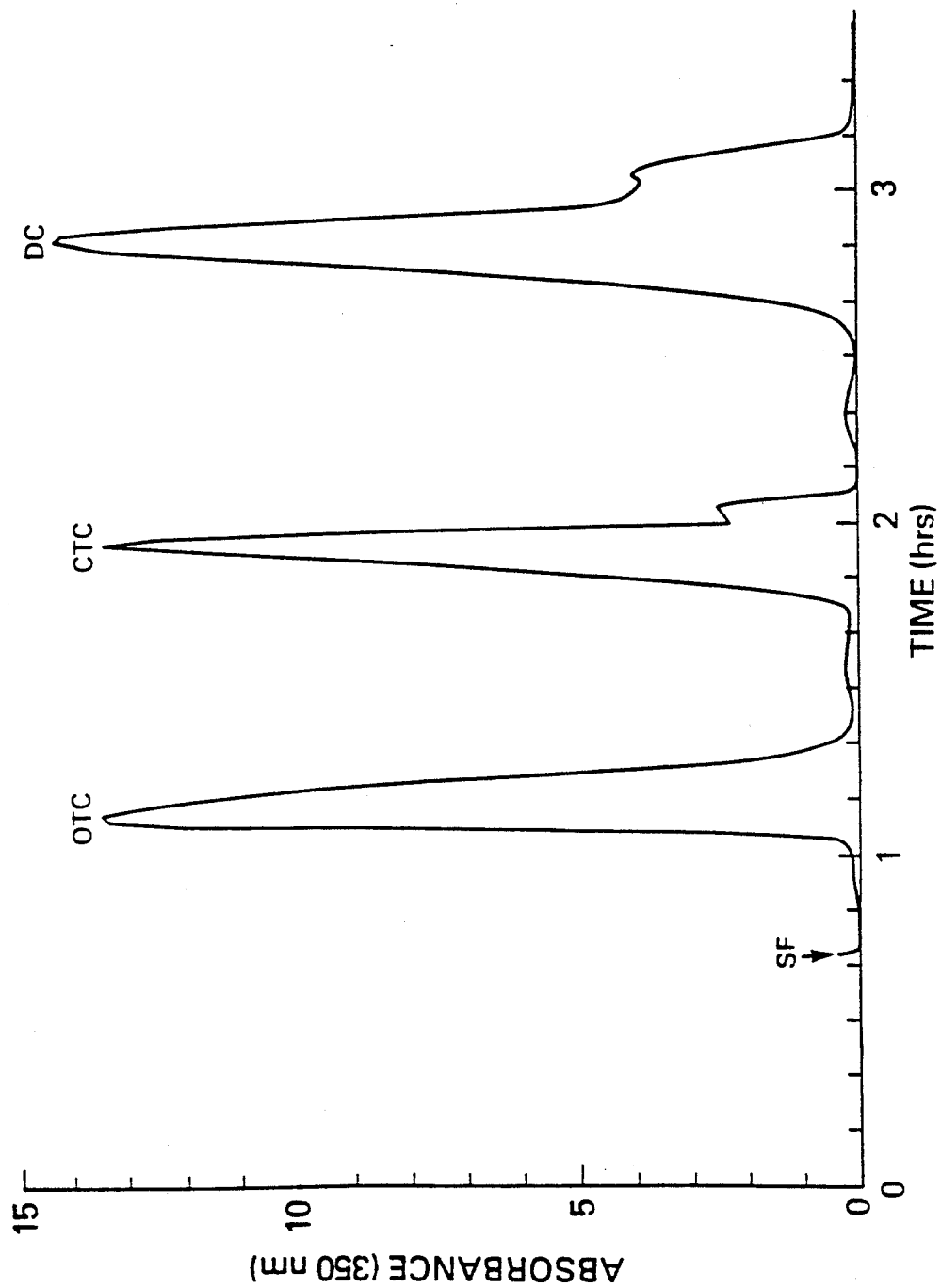

FIG. 3 shows a chromatogram of tetracycline derivatives obtained with a two-phase solvent system composed of ethyl acetate-n-butanol-0.25 M ammonium acetate (1:1:2, v/v/v). The lower aqueous phase was eluted at a flow rate of 150 ml/h under a revolutional speed of 1,250 rpm. Three components were well separated in slightly over 3 hours at partition efficiencies ranging from 380 TP (first peak) to 1,400 TP (third peak). The low partition efficiency of the first peak may be a result of an unresolved impurity hidden on the right side of the main peak as indicated by the asymmetry of the peak shape.

EXAMPLE 4

In order to demonstrate the versatility of the present high-speed CCC method, separation of three rare earth elements, LaCl$_3$, PrCl$_3$ and NdCl$_3$, was performed on the basis of their affinity to the ligand DEHPA, which is totally retained in the stationary heptane phase.

Figure 4:
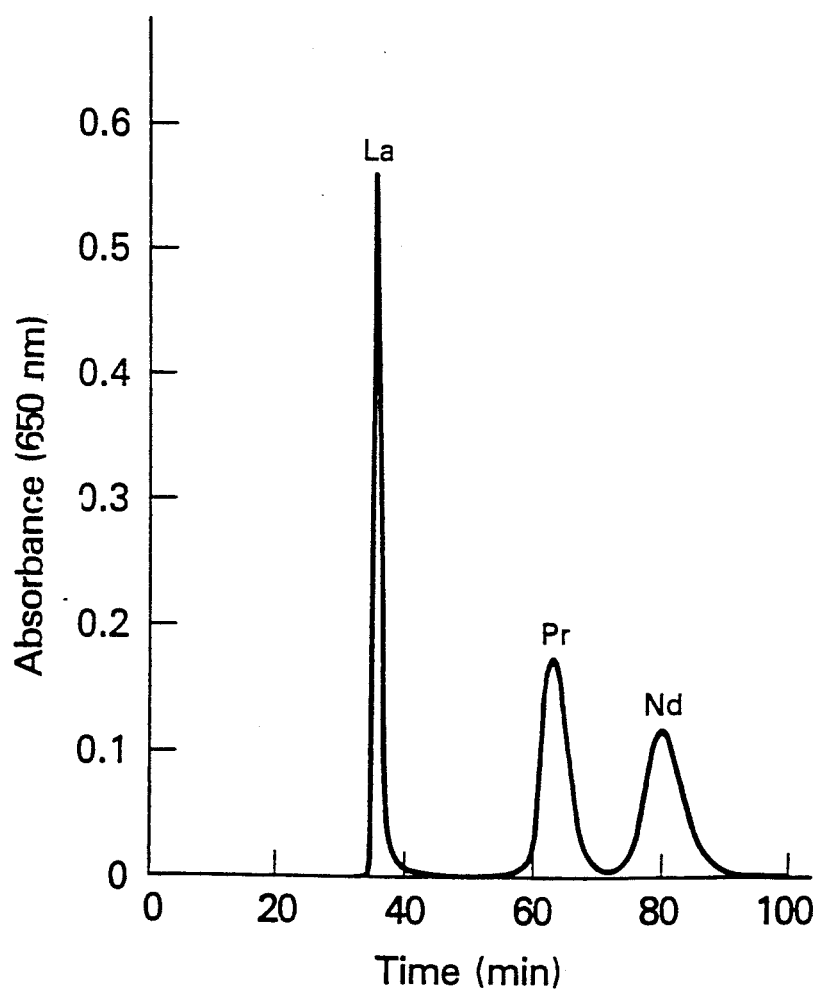

FIG. 4 shows a chromatogram of the three lanthanides obtained with a two-phase solvent system composed of 0.02 M DEHPA in n-heptane and 0.02 M hydrochloric acid. The separation was performed by eluting the lower aqueous phase at 300 ml/h under a revolutional speed of 900 rpm. Three components were well resolved within 1½ hours with partition efficiencies of 6,300 TP for the first peak (La), 1,100 TP for the second peak (Pr) and 780 TP for the third peak (Nd). These figures represent over one order of magnitude greater than those obtained by the centrifugal partition chromatograph with the same solvent system. The peak resolutions, $R_s$, computed from Eq 2 are 5.83 between the first and the second peaks and 1.82 between the second and the third peaks. The complete separation ($R_s \geq 1.5$) between Pr and Nd, which was difficult even at the raised ambient temperature of 55° C. with a modified ligand (2-ethylhexyl) phosphonic acid mon-2-ethylhexyl ester), was achieved at room temperature in a much shorter elution time.

In a further experiment, employing a similar procedure, 14 rare earth elements were separated in about 3 hours utilizing an exponential gradient elution of HCl.

EXAMPLE 5

Figure 5:
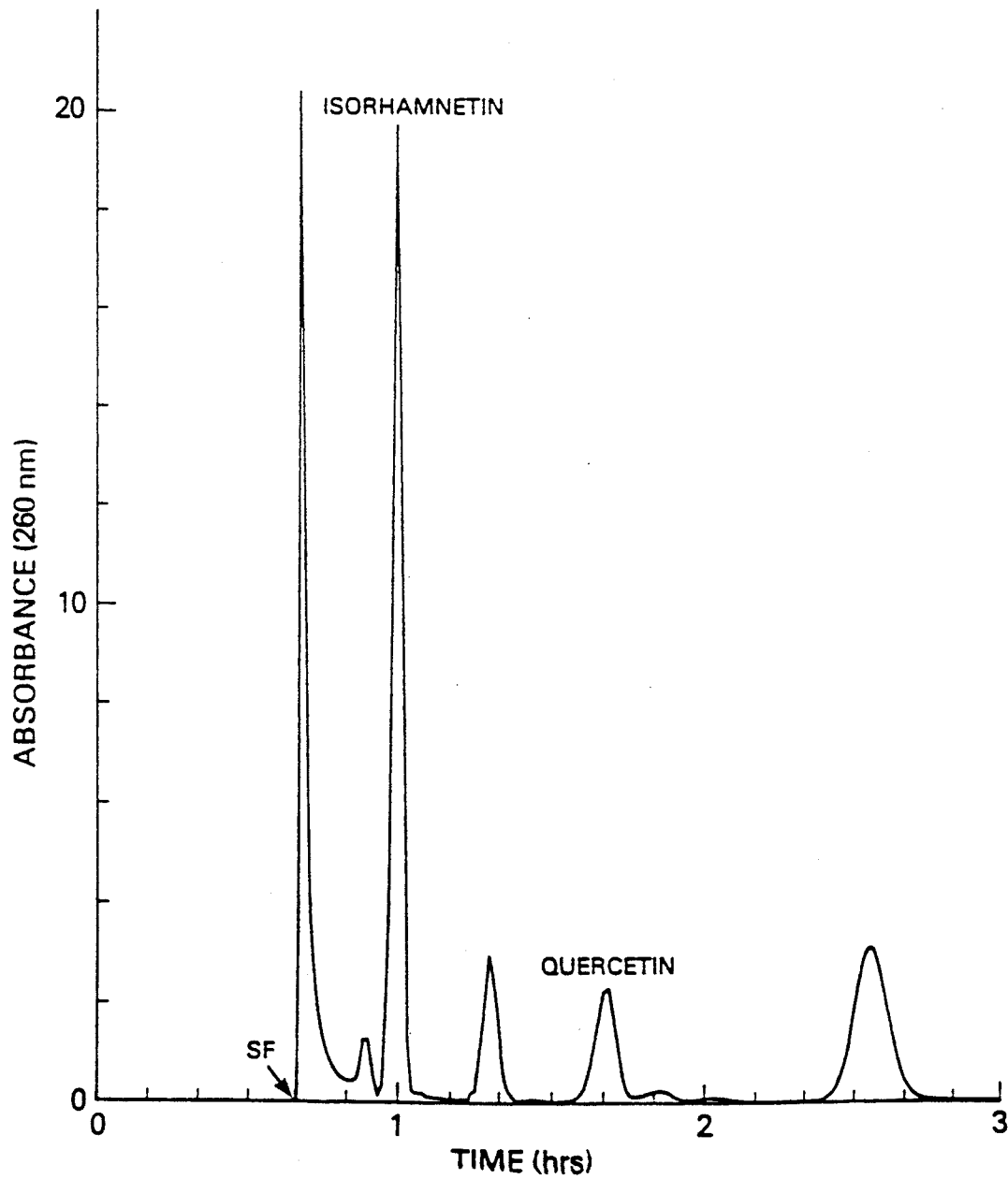

In this example, flavonoids from sea buckthorn extract were separated. FIG. 5 shows a chromatogram of flavonoids from a crude ethanol extract of sea buckthorn (*Hippophae rhamnoides*) obtained with a two-phase solvent system composed of chloroform-methanol-water (4:3:2, v/v/v). Separation was performed with the lower nonaqueous phase eluted at 180 ml/h under a revolutional speed of 1,200 rpm. A 100 mg quantity of the sample dissolved in 4.8 ml of the solvent mixture was separated into multiple peaks within 3 hours. The partition efficiency of the second peak (isorhamnetin) was 4,000 TP and that of the fourth peak (quercetin) was 2,800 TP. This result shows a considerable improvement in peak resolution over those obtained from the 1.5 mm I.D. column and also with other CCC instruments.

EXAMPLE 6

In this example, Bacitracin (BC) was separated. Commercial BC consists of a group of peptides with a bacteriocidic activity and is currently used as feed additives for livestock throughout the world. It contains the major active component, BC-A, its oxidation product, BC-F and over 20 other minor components with unknown nature, as shown by a reversedphase HPLC analysis.

Figure 6:
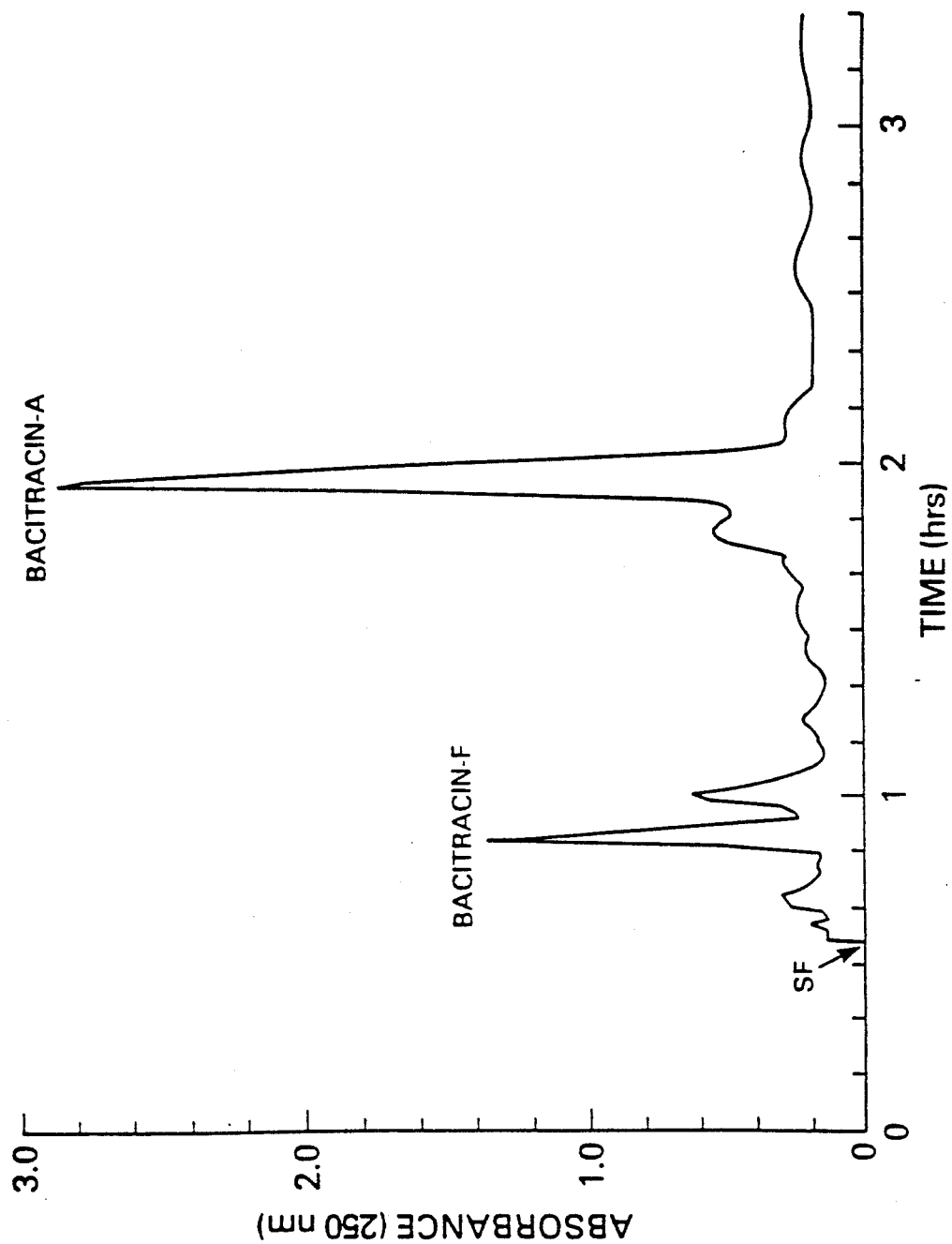

FIG. 6 shows a CCC separation of BC with a two-phase solvent system composed of chloroform-95% ethanol-water (5:4:3, v/v/v). The lower nonaqueous phase was used as the mobile phase at a flow rate of 150 ml/h at 1,200 rpm. A 100 mg sample quantity dissolved in 4.8 ml of the phase mixture was separated into multiple peaks. Partition efficiency of the major peak (BC-A) was 2,900 TP and that of the second peak (BC-F) was 2,700 TP.

EXAMPLE 7

Figure 7:
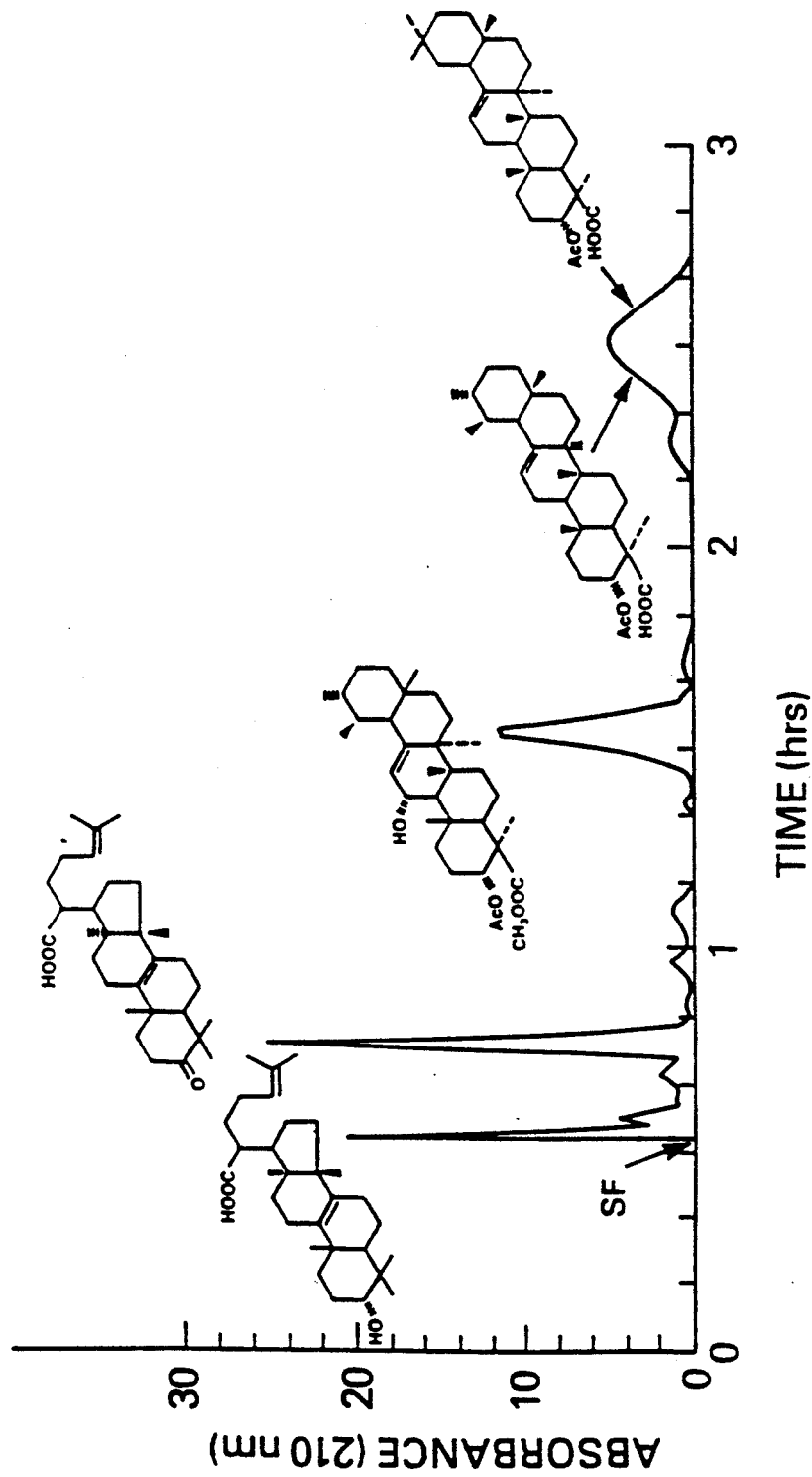

In this example, several Triterpenoic acids were separated. FIG. 7 shows a high-speed counter-current chromatogram of triterpenoic acids, extracted from *Boswellia carterii*, with a two-phase solvent system composed of n-hexane-95% ethanol-water (6:5:1, v/v/v). Separation was performed with the lower aqueous mobile phase being eluted at a flow rate of 150 ml/h and at a revolutional speed of 1,200 rpm. A crude extract (100 mg) dissolved in 2 ml of the upper nonaqueous phase was separated into multiple peaks. A similar chromatogram was obtained previously with a 1.6 mm I.D. column. Partition efficiencies of the second and third peaks were both 2,100 TP. As revealed by HPLC analysis of the fractions, the fourth peak contains a mixture of two isomers which were only partially resolved under the present CCC condition.

The overall results of the present studies clearly demonstrate the high performance capabilities of the present system. Sample quantities ranging from submilligram to 100 mg were successfully separated within a few hours. The new system regularly provided partition efficiencies of up to several thousand theoretical plates.

Although the present invention has been described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims which follow.

We claim:

1. A method of separating rare earth elements and compounds from a mixture containing the same which comprises subjecting said mixture to high-speed rotational countercurrent chromatography utilizing a planet coil centrifuge to thereby separating said rare earth elements and compounds.

2. A method of separating rare earth elements and compounds from mixtures containing the same according to claim 1, wherein a two phase solvent is utilized which comprises n-heptane containing di(2-ethylhexyl) phosphoric acid, and hydrochloric acid.

3. A method of separating rare earth elements and compounds from mixtures containing the same according to claim 2, wherein partition coefficients of the rare earth elements and compounds are optimized by adjusting hydrochloric acid concentration.

4. A method of separating rare earth elements and compounds from mixtures containing the same according to claim 2, wherein the concentration of said di(2-ethylhexyl) phosphoric acid is about 0.02 M and the concentration of said hydrochloric acid is about 0.02 M.

5. A method of separating rare earth elements and compounds from mixtures containing the same according to claim 1, wherein a two phase solvent is utilized which comprises n-heptane containing 2-ethylhexyl phosphoric acid mono-2-ethylhexyl ester, and hydrochloric acid.

6. A method of separating rare earth elements and compounds from mixtures containing the same according to claim 1, wherein said rare earth elements are selected from the group consisting of La, Pr and Nd.

7. A method of separating rare earth elements and compounds from mixtures containing the same according to claim 1, wherein prior to separation, the chromatography column is filled with said n-heptane containing di(2-ethylhexyl) phosphoric acid, thereafter a sample mixture containing at least one rare earth element is injected into said column and thereafter said hydrochloric acid is passed through said column at about 300 ml/hr.

8. A method of analyzing for rare earth elements and compounds in a mixture containing the same which comprises subjecting said mixture to high-speed rotational countercurrent chromatography utilizing a planet coil centrifuge to thereby separate said rare earth elements and continuously detecting for said separated rare earth elements and compounds.

9. A method for analyzing for rare earth elements and compounds in a mixture containing the same according to claim 8, wherein eluted rare earth elements and compounds are reacted in a post-column reaction with arsenazo III and said detection comprises on-line monitoring with a spectrophotometer.

10. A method for analyzing for rare earth elements and compounds in a mixture containing the same according to claim 9, wherein said monitoring is conducted at about 650 nm.

11. A method for analyzing for rare earth elements and compounds in a mixture containing the same according to claim 9, wherein said arsenazo III comprises 0.014 % w/v arsenazo in an ethanol solution.

12. A method for analyzing for rare earth elements and compounds in a mixture containing the same according to claim 10, wherein said post-column reaction included heating the reaction mixture to about 40° C.

13. A method for analyzing for rare earth elements and compounds in a mixture containing the same according to claim 8, wherein said separation utilizes a two phase solvent is utilized which comprises n-heptane containing di(2-ethylhexyl) phosphoric acid, and hydrochloric acid.

14. A method for analyzing for rare earth elements and compounds in a mixture containing the same according to claim 13, wherein the concentration of said di(2-ethylhexyl) phosphoric acid was about 0.02 M and the concentration of said hydrochloric acid was about 0.02.M.

15. A method for analyzing for rare earth elements and compounds in a mixture containing the same according to claim 8, wherein said rare earth elements are selected from the group consisting of La, Pr and Nd.

* * * * *